United States Patent [19]

Le

[11] Patent Number: 4,696,938

[45] Date of Patent: Sep. 29, 1987

[54] INSECTICIDAL 6-ARYL-PYRIDINE THIOSEMICARBAZONES

[75] Inventor: Dat P. Le, North Wales, Pa.

[73] Assignee: Rohm and Haas Company, Philadelphia, Pa.

[21] Appl. No.: 856,629

[22] Filed: Apr. 25, 1986

[51] Int. Cl.[4] .................. C07D 401/12; A61K 31/44; A61K 31/445

[52] U.S. Cl. .................... 514/343; 514/318; 514/336; 514/338; 546/194; 546/281; 546/268; 546/270

[58] Field of Search ............... 546/194, 281, 268, 270; 514/318, 336, 338, 343

[56] References Cited

U.S. PATENT DOCUMENTS

| 4,317,776 | 3/1982 | Klayman et al. | 544/360 |
|---|---|---|---|
| 4,405,791 | 9/1983 | Rutter et al. | 546/316 |
| 4,493,930 | 1/1985 | Klayman et al. | 544/360 |

FOREIGN PATENT DOCUMENTS

| 153340 | 3/1985 | European Pat. Off. | 546/331 |
|---|---|---|---|
| 135713 | 4/1985 | European Pat. Off. | 544/124 |

OTHER PUBLICATIONS

DeMilo et al., *J. Agric. Food Chem.*, 31, 713 (1983), "2-Acetylpyridine Thiosemicarbazones as Inhibitors of Ecdysis in Oncopeltus Fasciatus".
Kelly et al., *Pestic. Biochem. Physiol.*, 17, 35 (1982), "Inhibition of Ecdysis in Oncopeltus Fasciatus by 2-Acetylpyridine Thiosemicarbazones".
Klayman et al., *J. Pharm. Sci.*, 73, 1763, (1984), "2-Acetylpyridine Thiosemicarbazones XI".
Scovill et al., *J. Med. Chem.*, 27, 87 (1984), "2-Acetylpyridine Thiosemicarbazones".
*J. Med. Chem.*, 22, 855 (1974).
Pedersen et al., Pest. Sci., 25, 462 (1984), "Synthesis and Insect Growth Regulating Activity of Thiosemicarbazones of Methyl 2-Pyridyl Ketones.
Agrawal et al., *J. Med. Chem.*, 17, 631 (1974), "Potential Antitumor Agents".
Chen et al., *Bull. Inst. Chem. Acad. Sin.*, 25, 113 (1978), "Studies on Potential Antitumor Agents (II)".
Chen et al., *Heterocycles*, 5, 239 (1976), "Studies on Potential Antitumor Agents (I)".

*Primary Examiner*—Alan L. Rotman
*Attorney, Agent, or Firm*—Douglas E. Winters; John C. Demeter

[57] ABSTRACT

This invention relates to novel insecticidal 6-aryl-pyridine-thiosemicarbazones, compositions containing those compounds, methods of using said compounds and compositions.

20 Claims, No Drawings

INSECTICIDAL 6-ARYL-PYRIDINE THIOSEMICARBAZONES

BACKGROUND OF THE INVENTION

This invention relates to 6-aryl-pyridine thiosemicarbazones which are useful as insecticides, compositions containing those compounds, methods of using said compounds and compositions.

The search for compounds which have a combination of excellent insecticidal activity and low undesirable toxicity is a continuing one because of factors such as the desire for compounds exhibiting greater activity, better selectivity, low undesirable environment impact and effectiveness against insects resistant to many known insecticides.

Compounds of the present invention are particularly suitable for controlling plant-destructive insects in crops of cultivated plants, ornamentals and forestry.

Certain pyridine thiosemicarbazone derivatives have been disclosed in the literature.

In U.S. Pat. Nos. 4,317,776 and 4,493,930 certain 2-acetyl- and 2-propionylpyridine thiosemicarbazones which are substituted on the 4-nitrogen atom are disclosed. These compounds are useful as bactericides and antimalaria agents.

In *J. Agric. Food Chem.*, 1983, 31, 713–718, and Pesticide Biochem. and Physiol., 1982, 17, 35–41, certain 2-acetylpyridine thiosemicarbazones are disclosed as inhibitors of ecdysis.

In *J. of Pharm. Sci.*, 1984, 73, 1763–1767, certain 2-acetylpyridine thiosemicarbazones are disclosed as antimalarial and antibacterial agents.

In *J. Med. Chem.*, 1984, 27, 87–91, certain 2-acetylpyridine thiosemicarbazones are disclosed as potential antimalarial agents.

In *J. Med. Chem.*, 1979, 22, 855–862, certain 2-acetylpyridine thiosemicarbazones are disclosed as antimalarial agents.

In European Patent Application No. 153340-A, thiosemicarbazones of methyl 2-pyridyl ketones are disclosed as biocides.

In *Pest. Sci.*, 1984, 25, 462–470, certain thiosemicarbazones of methyl 2-pyridyl ketones are disclosed as having ecdysis inhibiting activity.

In *J. of Med. Chem.*, 1974, 17, 631–635, certain 2-formyl(m-amino)phenylpyridine thiosemicarbazones are disclosed as antineoplastic agents.

In U.S. Pat. No. 4,405,791, certain arylthioureido pyridinecarbamino compounds are disclosed as plant growth regulators.

In *Bull. Inst. Chem. Chin. Acad. Sci.*, 1978, 25, 113–131, certain thiosemicarbazones of 4-bromophenyl- and 2-chlorophenylpyridine-2-carboxaldehydes are disclosed as having antineoplastic activity.

The 6-aryl-pyridine thiosemicarbazones of the present invention differ from known compounds primarily by their 6-position substituent on the pyridine ring.

Compounds of the present invention are also distinguished by their insecticidal activity and selectivity against lepidopteran larvae without material adverse impact on beneficial insects.

It is believed the compounds of the present invention exhibit anti-juvenile hormone activity. When the compounds of the present invention are consumed by larvae, said larvae undergo a premature lethal metamorphosis. This activity is believed to be unique to this class of compounds.

SUMMARY OF THE INVENTION

In accordance with the present invention, there are provided insecticidal compounds having the formula:

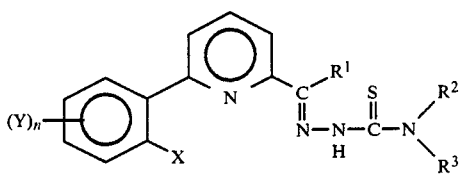

where
$R^1$ is hydrogen or methyl;
$R^2$ and $R^3$ taken together with the nitrogen atom to which they are attached to form a 3 to 6 membered heterocycle having 2 to 5 nuclear carbon atoms;
X is halo, nitro, $(C_1-C_4)$alkyl, $(C_1-C_4)$haloalkyl or $(C_1-C_4)$alkoxy;
Y is hydrogen, halo, $NO_2$, $(C_1-C_4)$alkyl or $(C_1-C_4)$alkoxy; or when two adjacent positions on the phenyl ring are substituted with alkoxy groups, these alkoxy groups may be joined to form a dioxolano or dioxano heterocyclic ring;
n is 0, 1 or 2;
or an agronomically acceptable salt thereof.

Also in accordance with the present invention there are provided compositions containing an insecticidally effective amount of a compound as defined above for Formula I and a agronomically acceptable carrier.

Further, in accordance with the present invention, there are provided methods of using these compounds and compositions.

DETAILED DESCRIPTION OF THE INVENTION

The term "halo" should be understood as including chloro, fluoro, bromo and iodo. The term "alkyl" by itself or as a part of another substituent, unless otherwise stated, includes straight and branched chain groups such as methyl, ethyl, n-propyl, isopropyl, n-butyl, sec-butyl, isobutyl and the like. The term "haloalkyl" by itself or as part of another substituent is an alkyl group of the stated number of carbon atoms having one or more halo atoms bonded thereto such as chloromethyl, 1- or 2-bromoethyl; trifluoromethyl and the like.

Typical compounds within the scope of the present invention include, but are not limited to:

6-(2-chlorophenyl)-2-formylpyridine-4-(pyrrolidin-1-yl)-thiosemicarbazone
6-(2-methylphenyl)-2-formylpyridine-4-(pyrrolidin-1-yl)-thiosemicarbazone
6-(2-bromophenyl)-2-formylpyridine-4-(pyrrolidin-1-yl)-thiosemicarbazone
6-(2-fluorophenyl)-2-formylpyridine-4-(pyrrolidin-1-yl)-thiosemicarbazone
6-(2-trifluoromethylphenyl)-2-formylpyridine-4-(pyrrolidin-1-yl)-thiosemicarbazone
6-(2,4-dichlorophenyl)-2-formylpyridine-4-(pyrrolidin-1-yl)-thiosemicarbazone
6-(2-chloro, 3-4-dioxolanophenyl)-2-formylpyridine-4-(pyrrolidin-1-yl)-thiosemicarbazone 6-(2-chlorophenyl)-2-acetylpyridine-4-(pyrrolidin-1-yl)-thiosemicarbazone 6-(2-bromophenyl)-2-acetylpyridine-4-(pyrrolidin-1-yl)-thiosemicarbazone 6-(2,4-dichlorophenyl)-2-acetylpyridine-4-(pyrrolidin-1-yl)-thiosemicarbazone 6-(2-chloro, 4-chloro-5-methoxyphenyl)-2-formylpyridine-4-(pyrrolidin-1-yl)-thiosemicarbazone 6-(2-chloro, 4-nitrophenyl)-2-formylpyridine-4-(piperidin-1-yl)-thiosemicarbazone 6-(2-chloro, 4-nitrophenyl)-2-acetylpyridine-4-(piperidin-1-yl)-thiosemicarbazone 6-(2-trifluoromethylphenyl)-2-acetylpyridine-4-(piperidin-1-yl)-thiosemicarbazone 6-(2,3,4-trichlorophenyl)-2-formylpyridine-4-(pyrrolidin-1-yl)-thiosemicarbazone.

Because of their insecticidal activity, preferred compounds of the present invention include those where, independently $R^1$ is hydrogen or methyl;

$R^2$ and $R^3$ are taken together with the nitrogen atom to which they are attached to form a 3 to 6 membered heterocycle having two to five nuclear carbon atoms;

X is halo or $(C_1-C_4)$alkyl;

Y is hydrogen;

n is 0;

and the agronomically acceptable salts thereof.

Because of their insecticidal activity, most preferred compounds of the present invention include those where, independently $R^1$ is hydrogen;

$R^2$ and $R^3$ are taken together with the nitrogen atom to which they are attached to form a pyrrolidinyl group;

X is halo or methyl;

Y is hydrogen;

n is 0;

and the agronomically acceptable salts thereof.

Those 6-aryl-pyridine thiosemicarbazones of Formula I which possess acidic or basic functional groups may be further reacted to form novel salts with appropriate bases or acids. These salts also exhibit pesticidal activity. Typical salts are the agronomically acceptable metal salts, ammonium salts and acid addition salts. Among the metal salts are those in which the metal cation is an alkali metal cation such as sodium, potassium, lithium or the like; alkaline earth metal cation such as calcium, magnesium, barium, strontium or the like; or heavy metal cation such as zinc, manganese, cupric, cuprous, ferric, ferrous, titanium, aluminum or the like. The ammonium salts include those in which the ammonium cation has the formula $NR^4R^5R^6R^7$ wherein each of $R^4$, $R^5$, $R^6$ and $R^7$ are independently hydrogen, hydroxy, $(C_1-C_4)$alkoxy, $(C_1-C_{20})$alkyl, $(C_3-C_8)$alkenyl, $(C_3-C_8)$alkynyl, $(C_2-C_8)$hydroxyalkyl, $(C_2-C_8)$alkoxyalkyl, $(C_2-C_6)$aminoalkyl, $(C_2-C_6)$haloalkyl, amino, $(C_1-C_4)$alkyl- or $(C_1-C_4)$dialkylamino, substituted or unsubstituted phenyl, substituted or unsubstituted phenylalkyl, having up to four carbon atoms in the alkyl moiety, or any two of $R^4$, $R^5$, $R^6$ or $R^7$ can be taken together to form with the nitrogen atom a 5- or 6-membered heterocyclic ring, optionally having up to one additional hetero atom (e.g., oxygen, nitrogen, or sulfur) in the ring, and preferably saturated, such as piperidino, morpholino, pyrrolidino, piperazino or the like, or any three of $R^4$, $R^5$, $R^6$ or $R^7$ can be taken together to form with the nitrogen atom a 5- or 6-membered aromatic heterocyclic ring, such as piperazole or pyridine. When $R^4$, $R^5$, $R^6$ or $R^7$ substituent in the ammonium group is a substituted phenyl or substituted phenylalkyl, the substituents on the phenyl and phenalkyl will generally be selected from halo, $(C_1-C_8)$alkyl, $(C_1-C_4)$alkoxy, hydroxy, nitro, trifluoromethyl, cyano, amino, $(C_1-C_4)$alkylthio and the like. Such substituted phenyl groups preferably have up to two such substituents. Representative ammonium cations include ammonium, dimethylammonium, 2-ethylhexylammonium, bis(2-hydroxyethyl)ammonium, tris(2-hydroxyethyl)ammonium, dicyclohexylammonium, t-octylammonium, 2-hydroxyethylammonium, morpholinium, piperidinium, 2-phenethylammonium, 2-methylbenzylammonium, n-hexylammonium, triethylammonium, trimethylammonium, tri(n-butyl)-ammonium, methoxyethylammonium, diisopropylammonium, pyridinium, dialkylammonium, pyrazolium, propargylammonium, dimethylhydrazinium, octadecylammonium, 4-dichlorophenylammonium, 4-nitrobenzylammonium, benzyltrimethylammonium, 2-hydroxy-ethyldimethyloctadecylammonium, 2-hydroxyethyldiethyloctylammonium, decyltrimethylammonium, hexyltriethylammonium, 4-methylbenzyltrimethylammonium, and the like. Among the acid addition salts are those in which the anion is an agronomically acceptable anion such as hydrochloride, hydrobromide, sulfate, nitrate, perchlorate, acetate, oxalate and the like.

The compounds of the present invention and their precursors can be made according to the following process.

Step 1:

Convert an omega-chloro-alkanone ethylene ketal of Formula II, for example 5-chloro-2-pentanone ethylene ketal or 6-chloro-3-hexanone ethylene ketal, to the corresponding Grignard reagent having the Formula III

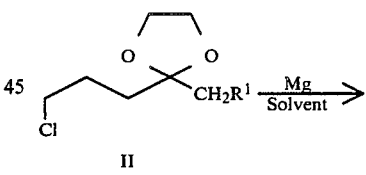

II

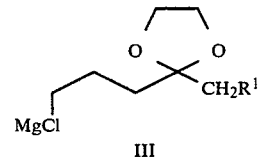

III

Step 2:

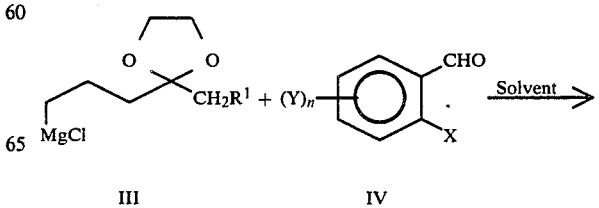

III IV

4,696,938
5
-continued
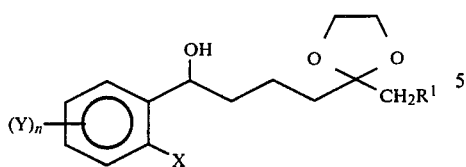
V
Step 3:
*Method A*
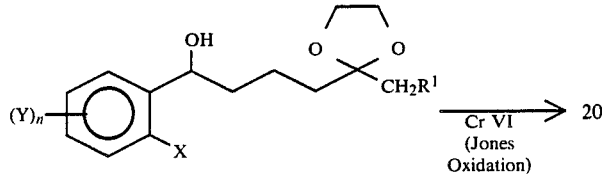
*Method B*
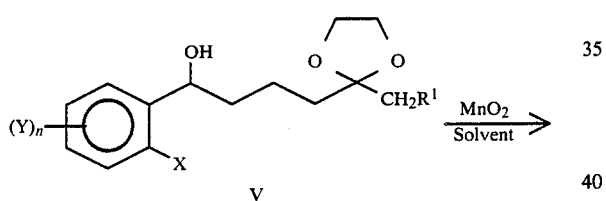
Step 4:
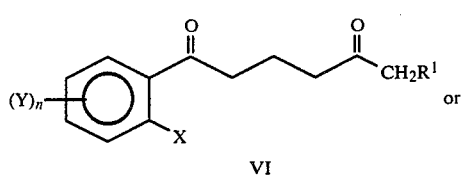
VI or
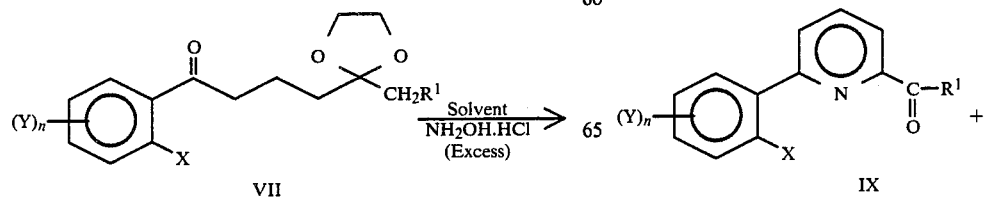
VII
6
-continued
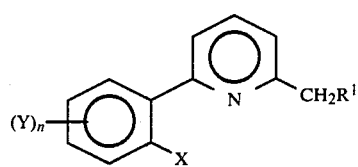
VIII
Step 5:
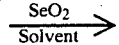
VIII
$\xrightarrow{\text{SeO}_2 / \text{Solvent}}$
IX
Step 6:
*Method A*
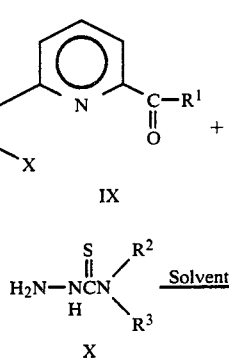
IX +
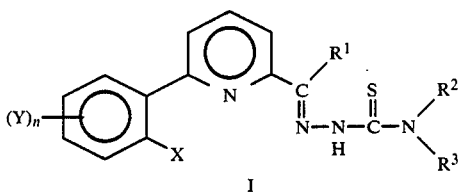
X
$\xrightarrow{\text{Solvent}}$
I
*Method B*
Stage 1:
IX +

-continued $$\underset{XI}{\underset{H}{H_2N-NCSCH_3}} \longrightarrow$$

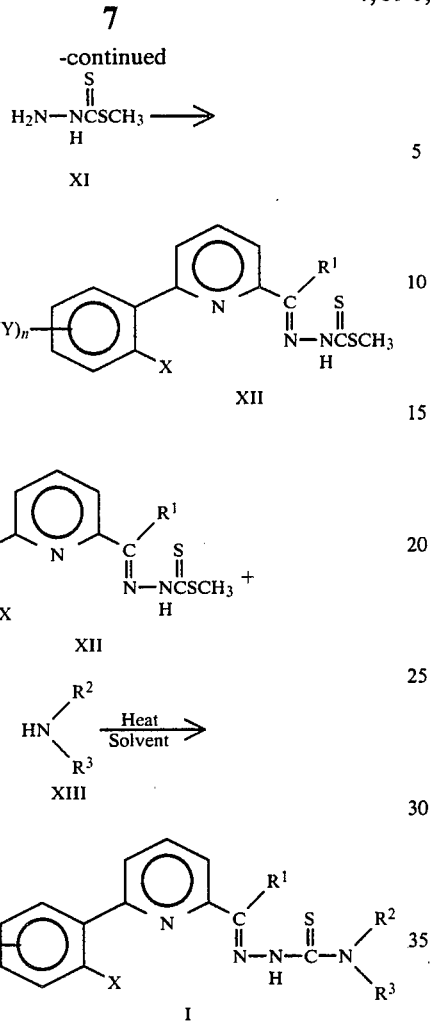

Stage 2:

where X, Y, n, $R^1$, $R^2$ and $R^3$ are as defined above for Formula I.

In Step 1, an omega-chloro-alkanone ethylene ketal having the Formula II, such as 5-chloro-2-pentanone ethylene ketal or 6-chloro-3-hexanone ethylene ketal is converted at a temperature below about 100° C. and preferably below about 70° C. to the corresponding Grignard reagent having the Formula III by procedures well known to those skilled in the art.

In Step 2, the Grignard reagent from Step 1 is reacted with a suitably substituted benzaldehyde of Formula IV at a temperature of from about −50° C. to about 50° C. and preferably from about −5° C. to about 10° C. in a suitable ethereal solvent such as diethyl ether or tetrahydrofuran (THF), preferably THF, to afford the alcohol of Formula V.

In Step 3, Method A, the alcohol of Formula V is subjected to a Jones oxidation (alcohol from Step 2 plus $CrO_3$ in water containing concentrated sulfuric acid) to afford a 1-aryl-1,5-alkanedione of Formula VI.

Alternatively, Step 3, Method B, where chromium reagents cannot be used, the alcohol of Formula V is treated with manganese dioxide in a halogenated hydrocarbon solvent such as dichloromethane, dichloroethane, chloroform or chlorobenzene, preferably dichloromethane, to afford a ketone of Formula VII.

In Step 4, the 1-aryl-1,5-alkanedione of Formula VI or the ketone of Formula VII is treated with excess hydroxylamine hydrochloride at a temperature of from about 50° C. to about 100° C., preferably from about 70° C. to about 80° C. in a polar solvent such as acetonitrile, methanol, ethanol or dimethylformamide, preferably acetonitrile, to afford a 6-aryl-2-alkylpyridine of Formula VIII. By "excess" hydroxylamine hydrochloride, it is meant generally from about 1.5 equivalents to about 5 equivalents, preferably from about 1.5 equivalents to about 2 equivalents, or hydroxylamine hydrochloride per equivalent of the 1-aryl-1,5-alkanedione of Formula VI or the ketone of Formula VII.

In Step 5, the 6-aryl-2-alkylpyridine of Formula VIII is treated with selenium dioxide in a suitable ethereal solvent such as tetrahydrofuran (THF) or 1,4-dioxane, preferably 1,4-dioxane to afford the compound of Formula IX.

In Step 6, Method A, the compound of Formula IX is reacted with the thiosemicarbazide of Formula X in a suitable solvent such as alcohols, preferably ethanol, to afford the 6-aryl-pyridine thiosemicarbazones of Formula I.

Alternatively, Step 6, Method B, the compound of Formula IX is reacted with a methyl hydrazinecarbodithioate of Formula XI in a suitable solvent such as alcohols, preferably isopropyl alcohol, to afford the compound of Formula XII. The compound of Formula XII is then reacted with the amine of Formula XIII in a suitable solvent, such as alcohols, preferably methanol, to afford the 6-aryl-pyridine thiosemicarbazones of Formula I.

The compounds of Formulae II, IV, X, XI and XIII are commercially available or can be prepared by known procedures.

Substantially equimolar amounts of reactants are preferably used in Steps 1 through 6 except Step 4 where an excess of hydroxylamine hydrochloride is employed, although higher or lower amounts can be used if desired.

Preferably, the above process is carried out at about atmospheric pressure, although higher or lower pressures can be used if desired.

Modifications to the above process may be necessary to accommodate reactive functionalities of particular substituents. Such modifications would be apparent and known to those skilled in the art.

The agronomically acceptable salts embraced by Formula I of the invention can be prepared by reacting a metal hydroxide, a metal hydride or an amine or ammonium salt, such as a halide, hydroxide or alkoxide with a compound of Formula I having one or more hydroxy or carboxy groups or reacting a quaternary ammonium salt, such as chloride, bromide, nitrate or the like with a metal salt of a compound of Formula I in a suitable solvent. When metal hydroxides are used as reagents, useful solvents include water; ethers such as glyme and the like; dioxane; tetrahydrofuran; alcohols such as methanol, ethanol, isopropanol and the like. When metal hydrides are used as reagents, useful solvents include nonhydroxylic solvents, for example, ethers such as dioxane, glyme, diethylether and the like; tetrahydrofuran; hydrocarbons such as toluene, xylene, hexane, pentane, heptane, octane and the like; dimethylformamide, and the like. When amines are used as reagents, useful solvents include alcohols, such as methanol or ethanol; hydrocarbons, such as toluene, xylene, hexane and the like; tetrahydrofuran; glyme; dioxane; or water. When ammonium salts are used as reagents, useful solvents include water; alcohols, such as methanol or ethanol; glyme; tetrahydrofuran; or the like.

When the ammonium salt is other than a hydroxide or alkoxide, an additional base, such as potassium or sodium hydroxide, hydride, or alkoxide is generally used. The particular choice of solvent will depend on the relative solubilities of the starting materials and the resultant salts, and slurries rather than solutions of certain reagents may be used to obtain the salts. Generally, equivalent amounts of the starting reagents are used and the salt-forming reaction is carried out at about 0° C. to about 100° C., preferably at about room temperature.

The acid addition salts of the present invention can be prepared by reacting hydrochloric, hydrobromic, sulfuric, nitric, phosphoric, acetic, propionic, benzoic or other suitable acid with a compound of Formula I having a basic functional group in a suitable solvent. Useful solvents include water, alcohols, ethers, esters, ketones, haloalkanes and the like. The particular choice of solvent will depend on the relative solubilities of the starting materials and the resulting salts and slurries rather than solutions of certain reagents may be used to obtain the salts. Generally, equivalent molar amounts of starting materials are used and the salt-forming reaction is carried out at from about −10° C. to about 100° C., preferably at about room temperature.

The following examples will further illustrate this invention but are not intended to limit it in any way. In Table I, some 6-aryl-pyridine thiosemicarbazones of the present invention that have been made are listed. The structure of these compounds was confirmed by NMR and in some cases by IR and/or elemental analysis. After Table I, preparation of certain reactants used in preparing the 6-aryl-pyridine thiosemicarbazones of the present invention are described as Examples A and B. Following Example B, specific illustrative preparation of the compounds of Examples 1–7 are described.

TABLE I

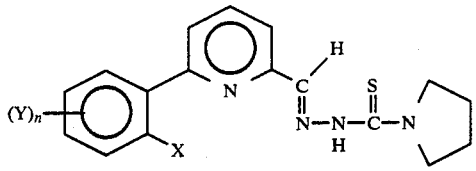

| Example No. | X | Y |
|---|---|---|
| 1 | Cl | H |
| 2 | CH$_3$ | H |
| 3 | Br | H |
| 4 | F | H |
| 5 | CF$_3$ | H |
| 6 | Cl | 4-Cl |
| 7 | Cl | 4,5-dioxolano |

EXAMPLE A

Preparation of Methyl Hydrazinecarbodithioate

Hydrazine hydrate (150 g) was added to a cooled (0° C.) solution of potassium hydroxide (197 g) in water (240 ml) and 2-propanol (200 ml). Pre-cooled carbon disulfide (182 ml) was then added dropwise to the stirred reaction mixture, maintaining internal temperature below 10° C. After the addition was complete, stirring was continued a further 1 hour. Cooled methyl iodide (426 g) was added dropwise over 1½ hours. The white precipitate was collected by filtration and washed with cooled water. The crude product was recrystallized from methylene chloride. m.p. 82° C.

EXAMPLE B

Preparation of Pyrrolidin-1-yl-thiosemicarbazide

Methyl hydrazinecarbodithioate (5 g) and pyrrolidine (3 g) were dissolved in 50 ml methanol and heated to reflux for 5 hours. After cooling the solid, pyrrolidin-1-yl-thiosemicarbazide was filtered, washed with methanol and air dried. m.p. 177°–178° C.

EXAMPLE 1

Preparation of 6-(2-chlorophenyl)-2-formyl pyridine-4-(pyrrolidin-1-yl)-thiosemicarbazone 5-chloro-2-pentanone ethylene ketal (0.0665 mol, 10 ml) was added to a suspension of magnesium (0.075 mol, 1.8 g, cleaned with ethylene dibromide) in 10 ml tetrahydrofuran (THF) so as to maintain the internal reaction temperature below 60° C. After the addition was complete, the green-gray reaction mixture was heated to about 55° C. for a further 2 hours. After cooling to about 5° C. and addition of a further 10 ml THF, a solution of 3-chlorobenzaldehyde (0.05 mol, 9.2 g) in 10 ml THF was added so as to maintain the internal temperature below 10° C. After warming the mixture to room temperature, it was poured onto aqueous saturated ammonium chloride. Extraction with ether followed by drying of the extracts and evaporation of solvents afforded 18 g of a pale yellow oil.

The crude ketal-alcohol was dissolved in 200 ml of acetone, cooled to about 5° C. and treated with Jones reagent (30 ml). After the addition was complete, the heterogenous mixture was allowed to stand at room temperature for 1.5 hours. The acetone layer was decanted and the residue was extracted with ether. The combined organic extracts were washed with several portions of dilute ammonium hydroxide and then were dried. Evaporation of the solvents afforded 15 g of crude 1-aryl-1,5-hexanedione. The crude diketone was dissolved in 120 ml of acetonitrile and treated with hydroxylamine hydrochloride (0.06 mol, 4.2 g) and heated at 70°–80° C. for 16 hours. After cooling to room temperature, the mixture was partitioned between saturated aqueous sodium bicarbonate and ether. The aqueous layer was extracted with ether and the combined extracts were washed with water and dried to afford 6-(2-chlorophenyl)-2-methylpyridine.

4.2 g of 6-(2-chlorophenyl)-2-methylpyridine was dissolved in 100 ml dioxane, 1.8 g of selenium dioxide (Aldrich, Gold Label) was added and the mixture was refluxed for 16 hours. The solution was decanted, fresh selenium dioxide (1.8 g) was added and refluxing was continued for a further 4 days. The solids were filtered and 250 ml ether was added. The organic solution was washed five times with 50 ml H$_2$O, dried over magnesium sulfate. Evaporation afforded an oil which was filtered through silica gel eluting with 30% ether-hexane to afford 3.2 g of 6-(2-chlorophenyl)-2-pyridinecarboxaldehyde as a pale yellow solid.

0.6 of 6-(2-chlorophenyl)-2-pyridinecarboxaldehyde was dissolved in 4 ml isopropyl alcohol, treated with 0.5 g of methyl hydrazinecarbodithioate and stirred at 23° C. for 16 hours. The solids were filtered off and air dried. The solids, methyl 3-[1-(6-(2-chlorophenyl)-2-pyridyl)methylidene]-hydrazinecarbodithioate, were dissolved in 5 ml of methanol treated with 0.2 ml pyrrolidine and gently refluxed for 8 hours. On cooling, 6-(2-chlorophenyl)-2-formylpyridine-4-(pyrrolidin-1-yl)-thiosemicarbazone was obtained by filtration. The crude thiosemicarbazone was washed with cool ether/methanol and air dried to afford 0.5 g 6-(2-chlorophenyl)-2-formylpyridine-4-(pyrrolidin-1-yl)-thiosemicarbazone. m.p. 187°–188° C.

EXAMPLE 2

Preparation of 6-(2-methylphenyl)-2-formylpyridine-4-(pyrrolidin-1-yl)-thiosemicarbazone 6-(2-methylphenyl)-2-methylpyridine was prepared substantially according to the procedures of Example 1 for preparing 6-(2-chlorophenyl)-2-methylpyridine except 2-methylbenzaldehyde was used to afford 6-(2-methylphenyl)-2-methylpyridine.

2.8 g of 6-(2-methylphenyl)-2-methylpyridine was dissolved in 180 ml 1,4-dioxane, 1.4 g of selenium dioxide (Aldrich Gold Label) was added and the mixture refluxed for 36 hours. The solids were removed by filtration. Ether was added and the organic extracts washed five times with 100 ml water. After drying over magnesium sulfate and evaporation, 6-(2-methylphenyl)-2-pyridinecarboxaldehyde was afforded as a pale yellow oil (1.4 g).

0.5 g 6-(2-methylphenyl)-pyridinecarboxaldehyde was dissolved in 5 ml absolute ethanol and treated with 0.35 g of pyrrolidin-1-yl-thiosemicarbazide. After 3 hours at 23° C., the crude 6-(2-methylphenyl)-2-formylpyridine-4-(pyrrolidin-1-yl)-thiosemicarbazone was isolated by filtration. The crude solids were washed well with absolute ethanol and dried in air to afford 0.4 g of 6-(2-methylphenyl)-2-formylpyridine-4-(pyrrolidin-1-yl)-thiosemicarbazone. m.p. 172°–173° C.

EXAMPLE 3

Preparation of 6-(2-bromophenyl)-2-formylpyridine-4-(pyrrolidin-1-yl)-thiosemicarbazone 6-(2-bromophenyl)-2-methylpyridine was prepared substantially according to the procedure of Example 1 for preparing 6-(2-chlorophenyl)-2-methylpyridine except 2-bromobenzaldehyde was used to afford 6-(2-bromophenyl)-2-methylpyridine.

6-(2-bromophenyl)-2-methylpyridine (3.5 g) was dissolved in 150 ml 1,4-dioxane. Selenium dioxide (Aldrich, Gold Label, 2.0 g) was added and the mixture was refluxed for a total of 50 hours. The solids were removed by filtration and the mixture was diluted with ether. The solution was washed several times with water, dried over magnesium sulfate, filtered and evaporated to afford 2.0 g of crude 6-(2-bromophenyl)-2-pyridinecarboxaldehyde as a yellow semi-solid.

Crude 6-(2-bromophenyl)-2-pyridinecarboxaldehyde (1.0 g) was dissolved in 8 ml ethanol, treated with 0.3 g of pyrrolidin-1-ylthiosemicarbazide and stirred at 23° C. for 3 hours. The product was isolated by filtration and washed with methanol to afford 0.2 g of 6-(2-bromophenyl)-2-formylpyridine-4-(pyrrolidin-1-yl)-thiosemicarbazone as a tan solid. m.p. 157°–159° C.

EXAMPLE 4

Preparation of 6-(2-fluorophenyl)-2-formylpyridine-4-(pyrrolidin-1-yl)-thiosemicarbazone 6-(2-fluorophenyl)-2-methylpyridine was prepared substantially according to the procedures of Example 1 for preparing 6-(2-chlorophenyl)-2-methylpyridine except 2-fluorobenzaldehyde was used to afford 6-(2-fluorophenyl)-2-methylpyridine.

2.0 g of 6-(2-fluorophenyl)-2-methylpyridine was dissolved in 250 ml of 1,4-dioxane. Selenium dioxide (2.67 g, Aldrich Gold Label) was added and the mixture was refluxed for 6 days. The solids were removed by filtration and the dioxane was evaporated. The crude 6-(2-fluorophenyl)-2-pyridinecarboxaldehyde was purified by chromatography on silica gel to afford pure 6-(2-fluorophenyl)-2-pyridinecarboxaldehyde.

1.0 g of 6-(2-fluorophenyl)-2-pyridinecarboxaldehyde was dissolved in 20 ml isopropanol and treated with methylhydrazinecarbodithioate (slight excess). After stirring at 23° C. for 6 hours, methyl 3-[1-(6-(2-fluorophenyl)-2-pyridyl)methylidene]hydrazinecarbodithioate was isolated by filtration and purified by washing with isopropanol. m.p. 160°–162° C.

1.0 g of methyl 3-[1-(6-(2-fluorophenyl)-2-pyridyl)methylidene]hydrazinecarbodithioate was dissolved in 25 ml methanol containing 0.26 g pyrrolidine. The mixture was refluxed for 5 hours, cooled and 6-(2-fluorophenyl)-2-formylpyridine-4-(pyrrolidin-1-yl)-thiosemicarbazone was removed by filtration and purified by washing with methanol. m.p. 154°–155° C.

EXAMPLE 5

Preparation of 6-(2-trifluoromethylphenyl)-2-formylpyridine-4-(pyrrolidin-1-yl)-thiosemicarbazone 6-(2-trifluoromethylphenyl)-2-methylpyridine was prepared substantially according to the procedures of Example 1 for prearing 6-(2-chlorophenyl)-2-methylpyridine except 2-trifluoromethylbenzaldehyde was used to afford 6-(2-trifluoromethylphenyl)-2-methylpyridine.

0.6 g of 6-(2-trifluoromethylphenyl)-2-methylpyridine was dissolved in 50 ml of 1,4-dioxane, 0.43 g of selenium dioxide (Aldrich, Gold Label) was added and the mixture was refluxed for 48 hours. A further 0.7 g, selenium dioxide and 50 ml dioxane were added and refluxing was continued for a further 48 hours. The solids were removed by filtration and the dioxane evaporated to afford crude 6-(2-trifluoromethylphenyl)-2-pyridinecarboxaldehyde.

0.7 g of crude 6-(2-trifluoromethylphenyl)-2-pyridinecarboxaldehyde was dissolved in 10 ml ethanol and treated with 0.35 g of pyrrolidin-1-yl-thiosemicarbazide. After stirring the mixture at 23° C. for 6 hours, 6-(2-trifluoromethylphenyl)-2-formylpyridine-4-(pyrrolidine-1-yl)-thiosemicarbazone was isolated by filtration and purified by washing with ethanol. m.p. 142°–146° C.

EXAMPLE 6

Preparation of 6-(2,4-dichlorophenyl)-2-formylpyridine-4-(pyrrolidin-1-yl)-thiosemicarbazone 6-(2,4-dichlorophenyl)-2-methylpyridine was prepared substantially according to the procedures of Example 1 for preparing 6-(2-chlorophenyl)-2-methylpyridine except 2,4-dichlorobenzaldehyde was used to afford 6-(2,4-dichlorophenyl)-2-methylpyridine.

1.5 g of 6-(2,4-dichlorophenyl)-2-methylpyridine was dissolved in 200 ml of 1,4-dioxane and treated with 1.05 g of selenium dioxide (Aldrich, Gold Label). The mixture was refluxed for 72 hours. An additional 1.2 g of selenium dioxide was added and the mixture was heated a further 48 hours. The solids were removed by filtration and the dioxane was evaporated to afford crude 6-(2,4-dichlorophenyl)-2-pyridinecarboxaldehyde which was chromatographed on silica-gel to afford 1.5 g of 6-(2,4-dichlorophenyl)-2-pyridinecarboxaldehyde as a white solid.

0.5 g of 6-(2,4-dichlorophenyl)-2-pyridinecarboxaldehyde was dissolved in 15 ml of ethanol and treated with 0.29 g of pyrrolidin-1-yl-thiosemicarbazide. After stirring at 23° C. for 18 hours, 6-(2,4-dichlorophenyl)-2-formylpyridine-4-(pyrrolidin-1-yl)-thiosemicarbazone was isolated by filtration and purified by washing with methanol. m.p. 155°–156° C.

EXAMPLE 7

Preparation of 6-(2-chloro-4,5-dioxolanophenyl)-2-formylpyridine-4-(pyrrolidin-1-yl)-thiosemicarbazone 6-(2-chloro-4,5-dioxolanophenyl)-2-pyridinealdehyde was prepared substantially according to the procedures of Example 1 for preparing 6-(2-chlorophenyl)-2-pyridinealdehyde except 2-chloro-4,5-dioxolanobenzaldehyde was used to afford 6-(2-chloro-4,5-dioxolanophenyl)-2-pyridinecarboxaldehyde.

Crude 6-(2-chloro-4,5-dioxolanophenyl)-2-pyridinecarboxaldehyde (0.5 g) was dissolved in 4 ml ethanol, treated with 0.3 g of pyrrolidin-1-yl-thiosemicarbazide and stirred at 23° C. for 14 hours. The product 6-(2-chloro-4,5-dioxolanophenyl)-2-formylpyridine-4-(pyrrolidin-1-yl)-thiosemicarbazone was isolated by filtration and was washed with ethanol and dried to afford 0.4 g of tan powder. m.p. 153°–154° C.

As previously noted, the compounds of the present invention exhibit insecticidal activity and are selective against larvae of the order Lepidoptera.

In general, for the control of insects in agriculture, horticulture and forestry, the compounds of the present invention may be used at a dosage corresponding to from about 10 grams to about 10 kilograms of the active substance per hectare and from about 100 grams to about 5 kilograms per hectare of the active substance is preferred. The exact amount of dosage for a given situation can be routinely determined and depends on a variety of factors, for example, the substance used, the kind of insect, the formulation used, the state of the crop infested with the insect and the prevailing weather conditions. The term "insecticidal" as employed in the specification and claims of this application is to be construed as any means which adversely affects the existence or growth of the target insects. Such means can comprise a complete killing action, eradication, arresting in growth, inhibition, reducing in number or any combination thereof. The term "control" as employed in the specification and claims of this application is to be construed as meaning "insecticidal" or protecting plants from insect damage. By "insecticidally effective amount" is meant that dosage of active substance sufficient to exert insect "control."

The compounds of the present invention, for practical applications, can be utilized in the form of compositions or formulations. Examples of the preparation of compositions and formulations can be found in the American Chemical Society publication "Pesticidal Formulation Research," (1969), Advances in Chemistry Series No. 86, written by Wade Van Valkenburg; and the Marcel Dekker, Inc. publication "Pesticide Formulations," (1973), edited by Wade Van Valkenburg. In these compositions and formulations, the active substance or substances are mixed with conventional inert agronomically acceptable (i.e., plant compatible and/or pesticidally inert) diluents or extenders such as solid carrier material or liquid carrier material, of the type usable in conventional compositions or formulations. By agronomically acceptable carrier is meant any substance which can be used to dissolve, disperse or diffuse the active ingredient in the composition without impairing the active ingredient's effectiveness and which by itself has no significant detrimental effect on the soil, equipment, desirable plants or agronomic environment. If desired, conventional adjuvants such as surfactants, stabilizers, antifoam agents and antidrift agents may also be added.

Examples of compositions and formulations according to the invention are aqueous solutions and dispersions, oily solutions and oil dispersions, pastes, dusting powders, wettable powders, emulsifiable concentrates, flowables, granules, baits, invert emulsions, aerosol compositions and fumigating candles.

Wettable powders, pastes, flowables and emulsifiable concentrates are concentrated preparations which are diluted with water before or during use.

Baits are preparations generally comprising a food or other substance attractive to the target pest, that includes at least one lethal or non-lethal toxicant. Lethal toxicants kill the pest upon ingesting the bait while non-lethal toxicants change the behavior, feeding habits and physiology of the pest for the purpose of control.

The invert emulsions are mainly used for air application, where large areas are treated with a comparatively small amount of preparation. The invert emulsion may be prepared in the spraying apparatus shortly before, or even during, the spraying operation be emulsifying water in an oil solution or an oil dispersion of the active substance.

Compositions and formulations are prepared in a known manner, for instance by extending the active compounds with conventional dispersible liquid diluent carriers and/or dispersible solid carriers optionally with the use of carrier vehicle assistants, e.g., conventional surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g., dichlorodifluoromethane and trifluorochloromethane, as well as butane, propane, nitrogen and carbon dioxide; inert dispersible liquid diluent carriers, including inert organic solvents, such as aromatic hydrocarbons (e.g., benzene, toluene, xylene, alkyl naphthalenes, etc.), halogenated, especially chlorinated, aromatic hydrocarbons (e.g., chlorobenzenes, etc.), cycloalkanes (e.g., cyclohexane, etc.), paraffins (e.g., petroleum or mineral oil fractions), chlorinated aliphatic hydrocarbons (e.g., methylene chloride, chloroethylenes, etc.) vegetable oils (e.g., soybean oil, cottonseed oil, corn oil, etc.), alcohols (e.g., methanol, ethanol, propanol, butanol, glycol, etc.) as well as ethers and esters thereof (e.g., glycol monomethyl ether, etc.), amines (e.g., ethanolamine, etc.), amides (e.g., dimethyl formamide, etc.), sulfoxides (e.g., dimethyl sulfoxide, etc.), acetonitrile, ketones (e.g., acetone, methyl ethyl ketone, methyl isobutyl ketone, cyclohexanone, isophorone, etc.), and/or water; solid carriers including ground natural minerals, such as kaolins, clays, talc, chalk, quartz, attapulgite, montmorillonite or diatomaceous earth, and ground synthetic minerals, such as highly-dispersed silicic acid, alumina and silicates; solid carriers for granules includes crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. The following may be chiefly considered for use as conventional carrier vehicle assistants: emulsifying agents, such as cationic and/or nonionic and/or anionic emulsifying agents (e.g., polyethylene oxide esters of fatty acids, polyethylene oxide ethers of fatty alcohols, alkyl sulfates, alkyl sulfonates, aryl sulfonates, albumin hydrolysates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

If desired, it is possible to use colorants in compositions and formulations containing compounds of the present invention such as inorganic pigments, for example, iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The active compounds of the present invention may be employed alone or in the form of mixtures with one another and/or with such solid and/or liquid dispersible carrier vehicles and/or with other known compatible active agents, especially plant protection agents, such as other insecticides, arthropodicides, nematicides, fungicides, bactericides, rodenticides, herbicides, fertilizers, growth-regulating agents, synergists, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1% and 99% by weight, and preferably between about 1% and 75% by weight, of the mixture. Carrier composition mixtures suitable for direct application or field application generally contemplate those in which the active compound is used in an amount substantially between about 0.0001% and 5%, preferably between about 0.001% and 3%, by weight of the mixture. Thus the present invention contemplates overall formulations and compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant (e.g., a surface-active agent, such as an emulsifying agent and/or a dispersing agent), and an amount of the active compound generally, between about 0.0001% and about 99% by weight of the composition, preferably between about 0.001% and about 90% by weight of the composition, and more preferably between about 0.01% and about 75% by weight of the composition, which is effective for the purpose in question.

The active compounds can be applied as sprays by methods commonly employed, such as conventional high-gallonage hydraulic sprays, low gallonage sprays, ultra-low-volume sprays, airblast spray, aerial sprays, and dusts. If low volume applications are desired, a solution of the compound is usually used. In ultra-low-volume applications, a liquid composition containing the active compound is usually applied as a spray (e.g., mist) by means of atomizing equipment in finely divided form (average particle size of from about 50 to about 100 microns or less) using airplane crop spraying techniques. Typically only a few liters per hectare are needed and often amounts up to about 15 to 1000 g/hectare, preferably about 40 to 600 g/hectare are sufficient. With ultra-low-volume, it is possible to use highly concentrated liquid compositions with said liquid carrier vehicles containing from about 20 to about 95% by weight of the active compound.

Furthermore, the present invention contemplates methods of killing, combatting or controlling insects, which comprises contacting insects with a correspondingly combative or toxic amount (i.e., an insecticidally effective amount) of at least one active compound of the invention alone or together with a carrier vehicle (composition or formulation) as noted above. The term "contacting" as employed in the specification and claims of this application is to be construed as applying to at least one of (a) such insects and (b) the corresponding habitat thereof (i.e., the locus to be protected, for example, to a growing crop or to an area where a crop is to be grown) the active compound of this invention alone or as a constituent of a composition or formulation. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting and the like.

It will be realized, of course, that the concentration of the particular active compound utilized in admixture with the carrier vehicle will depend upon such factors as the type of equipment employed, method of application, area to be treated, types of insects to be controlled and degree of infestation. Therefore, in special cases it is possible to go above or below the aforementioned concentration ranges.

Granular preparations are produced for example, by taking up the active substance in a solvent and by using the resulting solution, as the case may be in the presence of a binder, to impregnate a granular carrier material, such as porous granules (for example, pumice and attaclay), or chopped tobacco stems or the like.

A granular preparation (frequently termed a "pellet") may alternatively be produced by compressing the active substance together with powdered minerals in the presence of lubricants and binders and by disintegrating and straining the composite to the desired grain size.

Dusts are obtainable by intimately mixing the active substance with an inert solid carrier material in a concentration of from about 1% to about 50% by weight. Examples of suitable solid carrier materials are talc, kaolin, pipe clay, diatomaceous earth, dolomite, gypsum, chalk, bentonite, attapulgite and colloidal $SiO_2$ or mixtures of these and similar substances. Alternatively organic carrier materials such as, for example, ground walnut shells may be used.

Wettable powders and flowables are produced by mixing from about 10 to about 99 parts by weight of a solid inert carrier such, for example, as the aforementioned carrier materials with from about 1 to about 80 parts by weight of the active substance optionally dissolved in a volatile solvent such as acetone, from about 1 to about 5 parts by weight of a dispersing agent such, for example, as the lignosulfonates or alkylnaphthalene sulfonates known for this purpose and preferably also from about 0.5 to about 5 parts by weight of a wetting agent, such as fatty alcohol sulfates, or alkylarylsulfonates of fatty acid condensation products. In the case of flowables, a liquid inert carrier such as water is also included.

To produce emulsifiable concentrates the active compound is dissolved or finely divided in a suitable solvent which preferably is poorly miscible with water, an emulsifier being added to the resulting solution. Examples of suitable solvents are xylene, toluene, high-boiling aromatic petroleum distillates, for example solvent naphtha, distilled tar oil and mixtures of these liquids. Examples of suitable emulsifiers are alkylphenoxypolyglycol ethers, polyoxyethylene sorbitan esters of fatty acids or polyoxyethylene sorbitol esters of fatty acids. The concentration of the active compound in these emulsifiable concentrates is not restricted within narrow limits and may vary between about 2% and about 50% by weight depending upon toxicant solubility. A suitable liquid highly concentrated primary composition other than an emulsifiable concentrate is a solution of the active substance in a liquid which is readily miscible with water, for example, acetone, to which solution a dispersant and, as the case may be, a wetting agent are added. When such a primary composition is diluted with water shortly before or during the spraying operation an aqueous dispersion of the active substance is obtained.

An aerosol preparation according to the invention is obtained in the usual manner by incorporating the active substance or a solution thereof in a suitable solvent in a volatile liquid suitable for use as a propellant such, for example, as a mixture of chlorine and fluorine derivatives of methane and ethane.

Fumigating candles or fumigating powders, i.e., preparations which when burning are capable of emitting a pesticidal smoke, are obtained by taking up the active substance in a combustible mixture which may, for example, comprise a sugar or a wood, preferably in the ground form, as a fuel, a substance to sustain combustion such, for example, as ammonium nitrate or potassium chlorate, and furthermore a substance for retarding combustion, for example kaolin, bentonite and/or colloidal silicic acid.

A bait preparation comprises a food or other substance attractive to pests, a carrier, the toxicant and may optionally include other substances commonly used in preparations of this kind, such as, a preservative to inhibit bacterial and fungal growth, a waterproofing agent to prevent disintegration under wet conditions and dyes or colorants as described above.

In addition to the aforementioned ingredients, the preparations according to the invention may also contain other substances commonly used in preparations of this kind.

For example, a lubricant, such as calcium stearate or magnesium stearate, may be added to a wettable powder or to a mixture to be granulated. Furthermore, there may, for example, be added "adhesives" such as polyvinylalcohol cellulose derivatives or other colloidal materials, such as casein, to improve the adherence of this pesticide to the surface to be protected.

Representative preparation of compositions and formulations including the compounds of the present invention are set forth below as Examples C through K by way of illustration but not limitation.

EXAMPLE C

| Ingredient | Granular %/wt. |
|---|---|
| Toxicant and toxicant impurities | 0.25 |
| Triton ® X-305 (binder) (Octylphenyl-30-ethylene oxide ethanol) | 0.25 |
| Agsorb ® 24/48 (diluent) (Montmorillonite clay) | 99.50 |

Preparation: The toxicant and Triton ®X-305 are dissolved into methylene chloride and the mixture is added to the Agsorb ® with continuous mixing. The methylene chloride is then allowed to evaporate.

EXAMPLE D

| Ingredient | Dust %/wt. |
|---|---|
| Toxicant and toxicant impurities | 1.0 |
| Talc | 99.0 |

Preparation: Toxicant is dissolved in excess acetone and the mixture is impregnated onto the talc. The acetone is then permitted to evaporate.

EXAMPLE E

| Ingredient | Wettable Powder %/wt. |
|---|---|
| Toxicant and toxicant impurities | 31.3 |
| Duponal ® WA Dry (wetter) (Sodium lauryl sulfate) | 2.0 |
| Reax ® 45A (dispersant) (Sodium lignin sulfonate) | 5.0 |
| Barden clay (diluent) | 31.7 |
| HiSil ® 233 (diluent) (Sodium silica) | 30.0 |

Preparation: The toxicant, optionally dissolved in a volatile solvent, is absorbed onto the Barden clay and HiSil ® carriers. The Duponal ® and Reax ® are then added and the entire dry mixture blended until homogeneous. The composition is then micronized to a fine particle size.

EXAMPLE F

| Ingredient | Emulsifiable Concentrate %/wt. |
|---|---|
| Toxicant and toxicant impurities | 15.0 |
| Sponto ® 232T (emulsifier) (Anionic and nonionic blend of the following surfactants: calcium dodecyl benzene sulfonate; and ethoxylated alkylphenol) | 6.0 |
| Sponto ® 234T (emulsifier) (Anionic and nonionic blend of the following surfactants: calcium dodecyl benzene sulfonate; and | 4.0 |

-continued

| Emulsifiable Concentrate | |
|---|---|
| Ingredient | %/wt. |
| ethoxylated alkylphenol) | |
| Cyclohexanone (solvent) | 22.5 |
| Tenneco ® 500-100 (solvent) | 52.5 |
| (Aromatic solvent mixture principally comprising xylene, cumene and ethyl benzene having a boiling point range of 290-345° F.) | |

Preparation: All ingredients are mixed together with continuous agitation until a homogeneous clear solution is obtained.

EXAMPLE G

| Aerosol | |
|---|---|
| Ingredient | %/wt. |
| Toxicant and toxicant impurities | 0.5 |
| Freon 12 | 99.5 |

Preparation: The components are mixed and packaged under pressure in a suitable container equipped with a release spray valve.

EXAMPLE H

| Fumigating Candle or Fumigating Powder | |
|---|---|
| Ingredient | %/wt. |
| Toxicant and toxicant impurities | 1.0 |
| Wood dust | 96.0 |
| Starch | 3.0 |

Preparation: Toxicant, wood dust, and starch are blended together and then molded into a candle using a small amount of water to activate the starch.

EXAMPLE I

| Bait | |
|---|---|
| Method A | |
| Ingredient | %/wt. |
| Toxicant and toxicant impurities | 1.00 |
| Wheat Bran (carrier and attractant) | 89.95 |
| Corn Syrup (attractant) | 7.00 |
| Corn Oil (attractant) | 2.00 |
| Kathon ® 4200 (preservative) (3-isothiazolone) | 0.05 |

Preparation: The corn oil and corn syrup are added to the wheat bran with adequate mixing. The toxicant and Kathon ® are premixed with excess acetone and this solution is added to the wheat bran base with continued mixing. The acetone is then permitted to evaporate.

| Method B | |
|---|---|
| Ingredient | %/wt. |
| Toxicant and toxicant impurities | 0.06 |
| Granulated Sugar (carrier and attractant) | 99.94 |

EXAMPLE J

Pellet

Same as Example I, Method A, with this addition: the bait composition is formed into ¼" diameter by ⅜" long pellets using a suitable die and press apparatus.

EXAMPLE K

| Flowable | |
|---|---|
| Ingredient | %/wt. |
| Toxicant and toxicant impurities | 31.3 |
| Duponal ® WA Dry (wetter) (Sodium lauryl sulfate) | 2.0 |
| Reax ® 45A (dispersant) (Sodium lignin sulfonate) | 5.0 |
| HiSil ® 233 (diluent) (Sodium silica) | 30.0 |
| Kelzan ® (thickener) (Xanthan gum) | 0.5 |
| Water | 31.2 |

Preparation: The toxicant is absorbed onto the HiSil ® carrier. The Duponal ® and Reax ® are then added and the entire dry mixture blended until homogeneous. The composition is then micronized to a fine particle size. The resulting powder is suspended in water and the Kelzan ® added.

Compositions and formulations according to the present invention may also include known pesticidal compounds. This expands the spectrum of activity of the preparations and may give rise to synergism.

The following known insecticidal, fungicidal and acaricidal compounds are suitable for use in such a combined preparation.

Insecticides such as:
Chlorinated hydrocarbons, for example, 2,2-bis(p-chlorophenyl)-1,1,1-trichloroethane and hexachloro-epoxyoctahydrodimethanonaphthalene;
Carbamates, for example, N-methyl-1-naphthylcarbamates;
Dinitrophenols, for example, 2-methyl-4,6-dinitrophenol and 2-(2-butyl)-4,6-dinitrophenyl-3,3-dimethylacrylate;
Organic phosphorus compounds, such as dimethyl-2-methoxy-3-carbonyl-1-methylvinyl phosphate, 0,0-diethyl-0-p-nitrophenylphosphorothioate; N-monomethylamide of 0,0-dimethyldithiophosphorylacetic acid;
Diphenylsulfides, for example, p-chlorobenzyl or p-chlorophenyl sulfide and 2,4,4',5-tetrachlorodiphenylsulfide;
Diphenylsulfonates, for example, p-chlorophenylbenzenesulfonate;
Methylcarbinols, for example, 4,4-dichloro-1-trichloromethylbenzhydrol;
Quinoxaline compounds, such as methylquinoxaline dithiocarbonate;
Amidines such as N'-(4-chloro-2-methylphenyl) N,N-dimethylformamidine;
Pyrethroids such as Allethrin;
Biologicals such as *Bacillus thuringiensis* preparations;
Organic tin compounds such as tricyclohexyltin hydroxide;
Synergists such as piperonyl butoxide.
Fungicides such as:
Organic mercury compounds, for example, phenylmercuryacetate and methylmercurycyanoguanide;

Organic tin compounds, for example, triphenyltin hydroxide and triphenyltin acetate;
Alkylenebisdithiocarbamates, for example, zinc ethylenebisthiocarbamate and manganese ethylenebisthiocarbamate; and
2,4-dinitro-6-(2-octyl-phenylcrotonate), 1-bis(dimethylamino)phosphoryl-3-phenyl-5-amino-1,2,4-triazole, 6-methylquinoxaline-2,3-dithiocarbonate, 1,4-dithioanthraquinone-2,3-dicarbonitrile, N-trichloromethylthiophthalimide, N-trichloromethylthiotetrahydrophthalimide, N-(1,1,2,2-tetrachloroethylthio)-tetrahydrophthalimide, N-dichlorofluoromethylthio-N-phenyl-N'-dimethylsulfonyldiamide and tetrachloroisophthalonitrile.

It is known that induction of precocious molting in silkworms by anti-juvenile homone type compounds results in raw silk characterized by its fine denier, high dry and wet strengths, knot-strength and Young's modulus. Further, the silk produced is softer and its crease recovery is improved. Bull. of Sericultural Experiment Station; Ministry of Agriculture, Forestry and Fishery, Yatabe, Ibaraki, Japan; Vol. 30, No. 1, p. 123 (1985). Because of the premature metamorphosis in Lepidoptera larvae induced by compounds of the present invention, it is believed said compounds may advantageously be used in the production of silk. The compositions and formulations described above may be employed for this purpose. When used in the production of silk, the compounds of the present invention may be used at a dosage corresponding to from about 0.1 microgram to about 1 microgram of the active substance per larvae.

BIOLOGICAL ACTIVITY

It has been found by biological evaluation that compounds according to the present invention have insecticidal activity and are capable of controlling larvae from the order Lepidoptera. One skilled in the art will known how to determine the activity of a given compound against a given insect and the dosage required to obtain general or selective insecticidal effects.

The compounds of the present invention in part affect the normal development of insects, particularly insects from the order Lepidoptera, by directly and/or indirectly influencing the moulting process.

More particularly, when the compounds of the present invention are consumed by larvae, such larvae undergo a premature, lethal metamorphosis. It is believed the compounds of the present invention exhibit anti-juvenile hormone activity. This activity is believed to be unique and helps to distinguish compounds of the present invention from known compounds.

As previously noted, the compounds of the present invention are particularly suitable for controlling plant destructive insects in crops of cultivated plants, such as, but not limited to, cotton, vegetables, corn and other cereals and the like; forestry, such as, but not limited to, birch, spruce, pine, fir and the like; and ornamental plants, flowers and trees. Compounds of the present invention are also particularly suitable for controlling insects destructive to stored commodities such as seeds and the like; fruit crops, such as, but not limited to fruit and/or citrus trees, raspberry bushes and the like.

In evaluating the pesticidal activity of the compounds of this invention, the following test procedures were employed.

Larvae of the tobacco budworm (*Heliothis viriscens F.*) were raised from the egg stage on commercially available black cutworm diet (from Bioserv, U.S.A.) at 26° C., 16 hours of light, 8 hours of darkness. Newly ecdysed penultimate instar budworms (4th instar) were fed the black cutworm diet into whcih the experimental compound had been incorporated by admixing a solution of the compound in 0.5 ml dimethyl sulfoxide/acetone (1:1) into 100 ml of the diet while it was fluid (65° C.). The test larvae were kept in individual containers. The budworms were observed after 10 days for morphological outcome, especially precocious pupal characteristics.

Initial evaluations were made on tobacco budworm fed an artificial diet which included the test compound at 100 parts per million (ppm).

The results of the initial insecticidal evaluations are given in Table II. The evaluations are based on a scale of 0–100 in which 0 equals no activity and 100 equals total premature metamorphosis. Such premature metamorphosis will result in death.

TABLE II

| Initial Biological Evaluations | |
| --- | --- |
| Example No. | Activity |
| 1 | 100 |
| 2 | 90 |
| 3 | 90 |
| 4 | 60 |
| 5 | 70 |
| 6 | 80 |
| 7 | 35 |

It should be understood that the instant specification and claims are set forth by way of illustration and not limitation and that various modifications and changes may be made without departing from the spirit and scope of the present invention as defined by the appended claims.

What is claimed is:

1. A compound having the formula

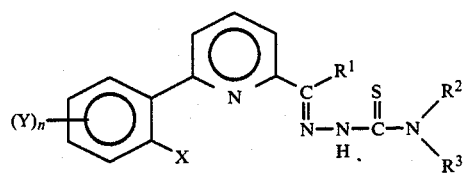

where
R$^1$ is hydrogen or methyl;
R$^2$ and R$^3$ taken together with the nitrogen atom to which they are attached form a 3 to 6 membered heterocycle having 2 to 5 nuclear carbon atoms;
X is halo, nitro, (C$_1$–C$_4$)alkyl, (C$_1$–C$_4$)haloalkyl or (C$_1$–C$_4$)alkoxy;
Y is hydrogen, halo, NO$_2$, (C$_1$–C$_4$)alkyl or (C$_1$–C$_4$)alkoxy; or when two adjacent positions on the phenyl ring are substituted with alkoxy groups, these alkoxy groups may be joined to form a dioxolano or dioxano heterocyclic ring;
n is 0, 1 or 2;
and the agronomically acceptable salts thereof.

2. A compound according to claim 1 wherein
R$^1$ is hydrogen or methyl;
R$^2$ and R$^3$ taken together with the nitrogen atom to which they are attached to form a 3 to 6 membered heterocycle having two to five nuclear carbon atoms;
X is halo or (C$_1$–C$_4$)alkyl;

Y is hydrogen;
n is 0;
or an agronomically acceptable salt thereof.

3. A compound according to claim 2 wherein
   $R^1$ is hydrogen
   $R^2$ and $R^3$ taken together with the nitrogen atom to which they are attached to form a pyrrolidinyl group;
   X is halo or methyl;
   Y is hydrogen;
   n is 0;
and the agronomically acceptable salts thereof.

4. A compound according to claim 3 wherein
   $R^1$ is hydrogen;
   $R^2$ and $R^3$ taken together with the nitrogen atom to which they are attached to form a pyrrolidinyl group;
   X is chloro;
   Y is hydrogen; and
   n is 0.

5. A compound according to claim 3 wherein
   $R^1$ is hydrogen;
   $R^2$ and $R^3$ taken together with the nitrogen atom to which they are attached to form a pyrrolidinyl group;
   X is methyl;
   Y is hydrogen; and
   n is 0.

6. A compound according to claim 3 wherein
   $R^1$ is hydrogen;
   $R^2$ and $R^3$ taken together with the nitrogen atom to which they are attached to form a pyrrolidinyl group;
   X is bromo;
   Y is hydrogen; and
   n is 0.

7. An insecticidal composition comprising an agronomically acceptable carrier and an insecticidally effective amount of a compound having the formula

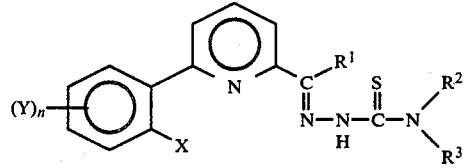

where
   $R^1$ is hydrogen or methyl;
   $R^2$ is $(C_1-C_4)$alkyl;
   $R^3$ is $(C_1-C_4)$alkyl; or
   $R^2$ and $R^3$ may be taken together with the nitrogen atom to which they are attached to form a 3 to 6 membered heterocycle having 2 to 5 nuclear carbon atoms;
   X is halo, nitro, $(C_1-C_4)$alkyl, $(C_1-C_4)$haloalkyl or $(C_1-C_4)$alkoxy;
   Y is hydrogen, halo, $NO_2$, $(C_1-C_4)$alkyl or $(C_1-C_4)$alkoxy; or when two adjacent positions on the phenyl ring are substituted with alkoxy groups, these alkoxy groups may be joined to form a dioxolano or dioxano heterocyclic ring;
   n is 0, 1 or 2;
and the agronomically acceptable salts thereof.

8. The composition according to claim 7 wherein
   $R^1$ is hydrogen or methyl;
   $R^2$ and $R^3$ are taken together with the nitrogen atom to which they are attached to form a 3 to 6 membered heterocycle having two to five nuclear carbon atoms;
   X is halo or $(C_1-C_4)$alkyl;
   Y is hydrogen;
   n is 0;
and the agronomically acceptable salts thereof.

9. The compositions according to claim 8 wherein
   $R^1$ is hydrogen
   $R^2$ and $R^3$ are taken together with the nitrogen atom to which they are attached to form a pyrrolidinyl group;
   X is halo or methyl;
   Y is hydrogen;
   n is 0;
and the agronomically acceptable salts thereof.

10. The composition according to claim 9 wherein said compound is 6-(2-chlorophenyl)-2-formylpyridine-4-(pyrrolidin-1-yl)-thiosemicarbazone.

11. The composition according to claim 9 wherein said compound is 6-(2-methylphenyl)-2-formylpyridine-4-(pyrrolidin-1-yl)-thiosemicarbazone.

12. The composition according to claim 9 wherein said compound is 6-(2-bromophenyl)-2-formylpyridine-4-(pyrrolidin-1-yl)-thiosemicarbazone.

13. A method of controlling insects which comprises contacting said insects with an insecticidally effective amount of a compound having the formula where
   $R^1$ is hydrogen or methyl;
   $R^2$ is $(C_1-C_4)$alkyl;
   $R^3$ is $(C_1-C_4)$alkyl; or
   $R^2$ and $R^3$ may be taken together with the nitrogen atom to which they are attached to form a 3 to 6 membered heterocycle having 2 to 5 nuclear carbon atoms;
   X is halo, nitro, $(C_1-C_4)$alkyl, $(C_1-C_4)$haloalkyl or $(C_1-C_4)$alkoxy;
   Y is hydrogen, halo, $NO_2$, $(C_1-C_4)$alkyl or $(C_1-C_4)$alkoxy; or when two adjacent positions on the phenyl ring are subsituted with alkoxy groups, these alkoxy groups may be joined to form a dioxolano or dioxano heterocyclic ring;
   n is 0, 1 or 2;
and the agronomically acceptable salts thereof.

14. The method of claim 13 wherein
   $R^1$ is hydrogen or methyl;
   $R^2$ and $R^3$ are taken together with the nitrogen atom to which they are attached form a 3 to 6 membered heterocycle having two to five nuclear carbon atoms;
   X is halo or $(C_1-C_4)$alkyl;
   Y is hydrogen;
   n is 0;
or an agronomically acceptable salt thereof.

15. The method of claim 14 wherein
   $R^1$ is hydrogen

R² and R³ are taken together with the nitrogen atom to which they are attached form a pyrrolidinyl group;

X is halo or methyl;

Y is hydrogen;

n is 0;

or an agronomically acceptable salts thereof.

16. The method of claim 15 wherein said insect is from the order Lepidoptera.

17. The method of claim 15 wherein said compound is 6-(2-chlorophenyl)-2-formylpyridine-4-(pyrrolidin-1-yl)-thiosemicarbazone.

18. The method of claim 15 wherein said compound is 6-(2-methylphenyl)-2-formylpyridine-4-(pyrrolidin-1-yl)-thiosemicarbazone.

19. The method of claim 15 wherein said compound is 6-(2-bromophenyl)-2-formylpyridine-4-(pyrrolidin-1-yl)-thiosemicarbazone.

20. A method of producing premature metamorphosis in Lepidoptera larvae by feeding said larvae an effective metamorphosis inducing amount of a compound having the formula

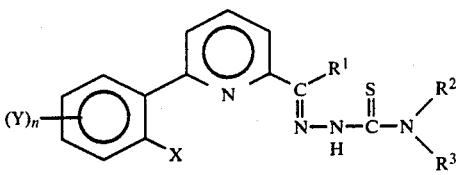

where
- $R^1$ is hydrogen or methyl;
- $R^2$ and $R^3$ may be taken together with the nitrogen atom to which they are attached form a 3 to 6 membered heterocycle having 2 to 5 nuclear carbon atoms;
- X is halo, nitro, $(C_1-C_4)$alkyl, $(C_1-C_4)$haloalkyl or $(C_1-C_4)$alkoxy;
- Y is hydrogen, halo, $NO_2$, $(C_1-C_4)$alkyl or $(C_1-C_4)$alkoxy; or when two adjacent positions on the phenyl ring are substituted with alkoxy groups, these alkoxy groups may be joined to form a dioxolano or dioxano heterocyclic ring;
- n is 0, 1 or 2;

or an agronomically acceptable salts thereof.

* * * * *